(12) United States Patent
Levy et al.

(10) Patent No.: US 7,789,900 B2
(45) Date of Patent: Sep. 7, 2010

(54) DOUBLE COLLET CONNECTOR ASSEMBLY FOR BONE ANCHORING ELEMENT

(75) Inventors: Mark M. Levy, Raanana (IL); Eyal Zylberberg, Kfar Yona (IL); Yair Spanier, Pardes Hanna (IL)

(73) Assignee: Expanding Orthopedics, Inc., Memphis, TN (US)

( * ) Notice: Subject to any disclaimer, the term of this patent is extended or adjusted under 35 U.S.C. 154(b) by 94 days.

(21) Appl. No.: 11/949,916

(22) Filed: Dec. 4, 2007

(65) Prior Publication Data

US 2009/0143827 A1 Jun. 4, 2009

(51) Int. Cl.
*A61B 17/04* (2006.01)
*A61B 17/70* (2006.01)

(52) U.S. Cl. ............. 606/300; 606/265; 606/267; 606/308

(58) Field of Classification Search ......... 606/300–321, 606/60, 151, 246–250, 257, 264–279
See application file for complete search history.

(56) References Cited

U.S. PATENT DOCUMENTS 5,882,350 A 3/1999 Ralph et al.
2006/0276792 A1* 12/2006 Ensign et al. ............ 606/61
2007/0049933 A1 3/2007 Ahn et al.
2007/0118123 A1* 5/2007 Strausbaugh et al. ...... 606/61

FOREIGN PATENT DOCUMENTS

FR 2796545 1/2001
WO 2006/116437 11/2006

* cited by examiner

*Primary Examiner*—Eduardo C Robert
*Assistant Examiner*—Christina Negrelli
(74) *Attorney, Agent, or Firm*—Dekel Patent Ltd.; David Klein

(57) ABSTRACT

A connector assembly including a bone anchoring element including a spherical head, a double collet that includes an inner clamping portion formed by inner surfaces of a plurality of resilient fingers, the resilient fingers defining a first wedge surface and a second wedge surface, an outer closure element that includes an inner clamping portion that corresponds in shape to an outer contour of the double collet, the outer closure element including a pair of arms that define a channel shaped for receiving therein a connector element, and an interface ring that includes a base formed with an inner wedge surface and a pair of wing extensions that extend from the base.

2 Claims, 5 Drawing Sheets

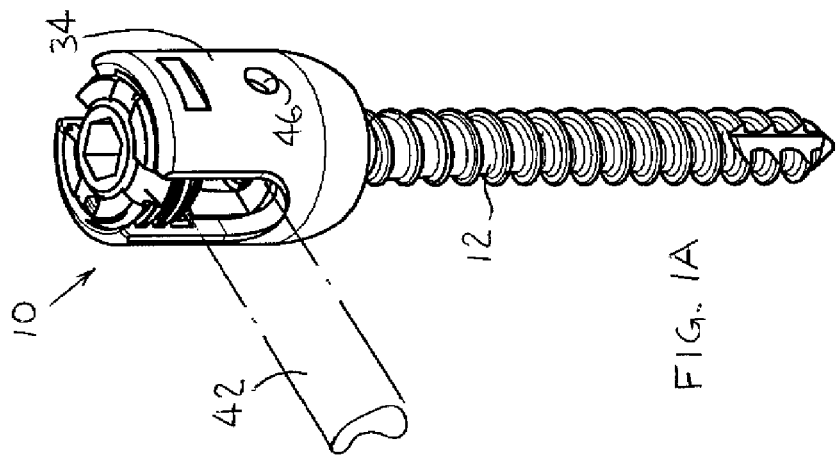
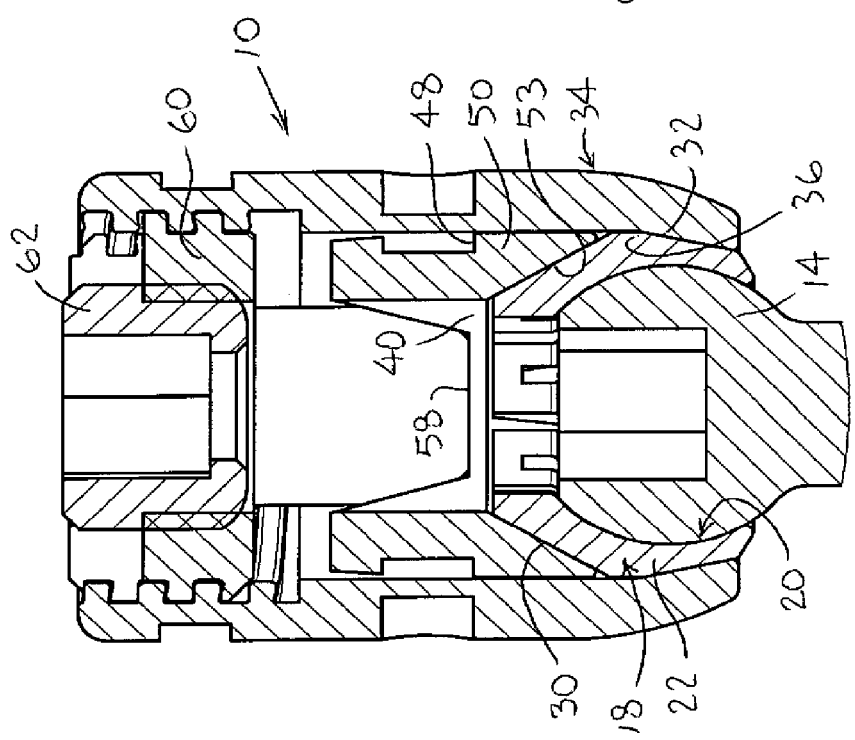
FIG. 1A
FIG. 1B

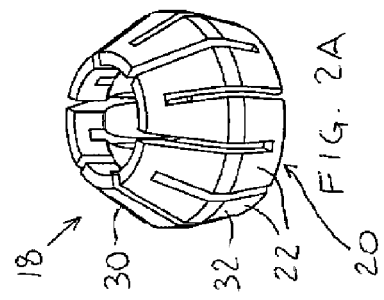
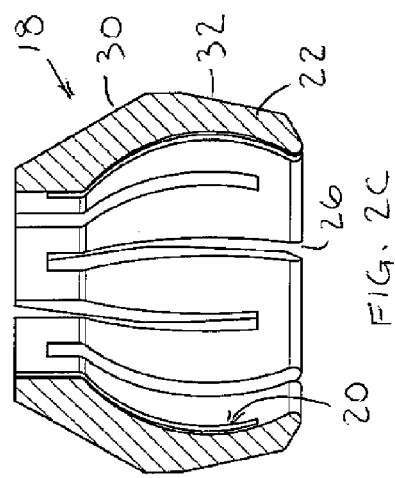
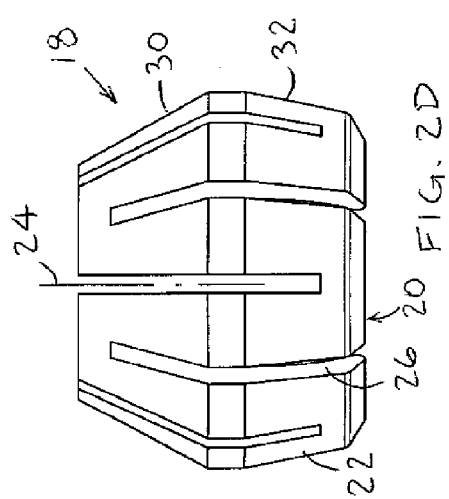
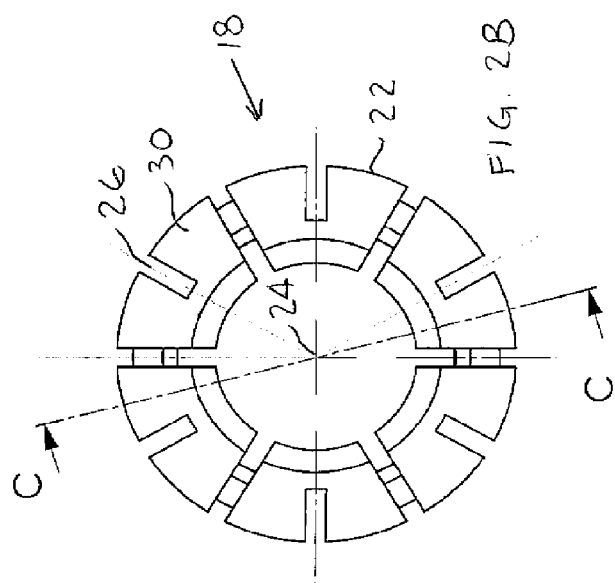

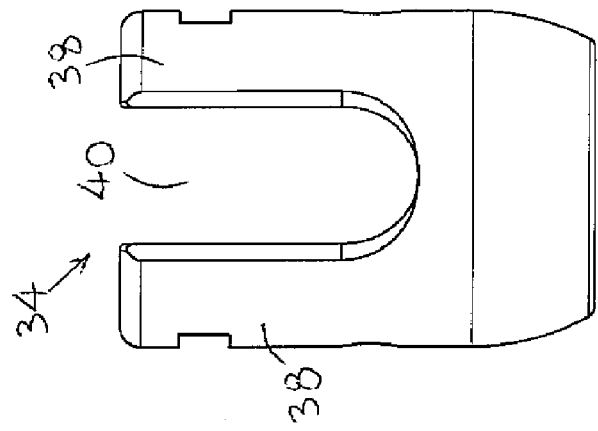
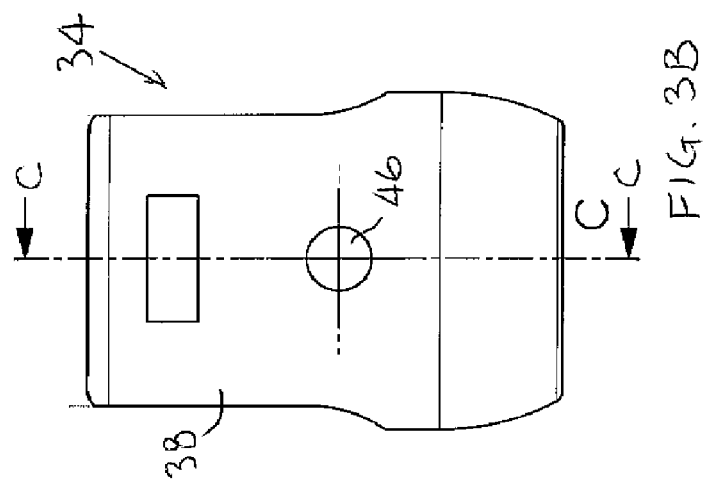
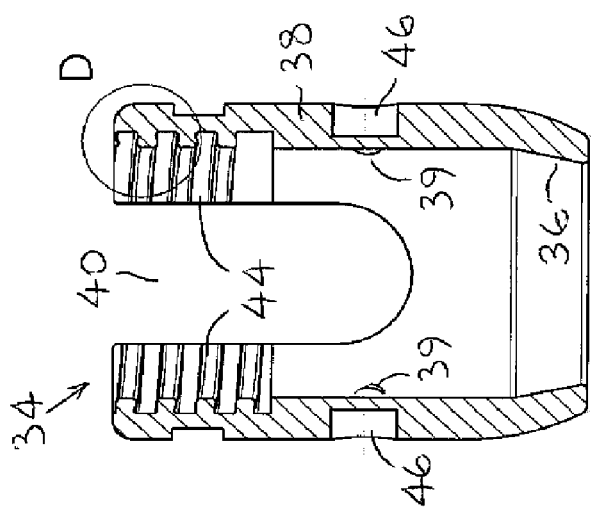
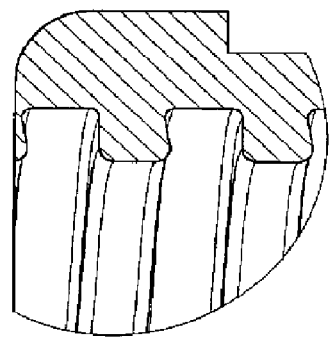

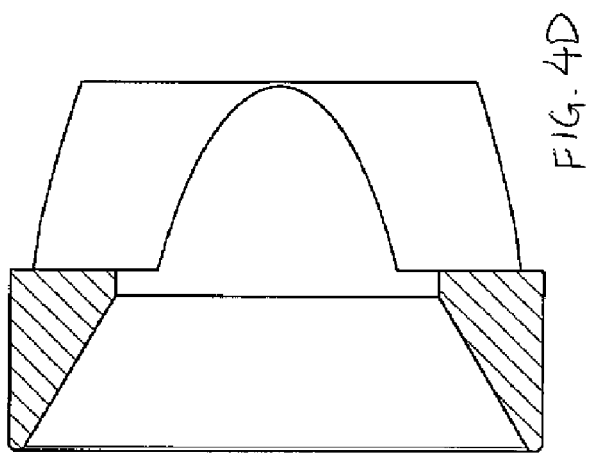
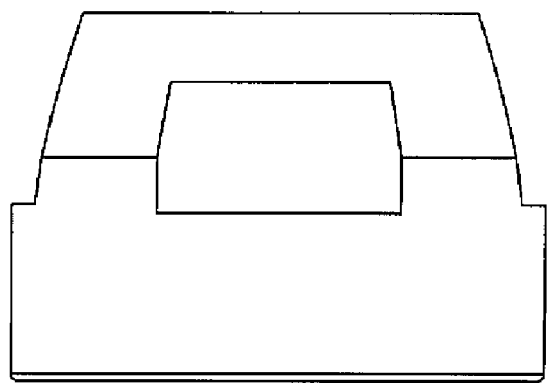
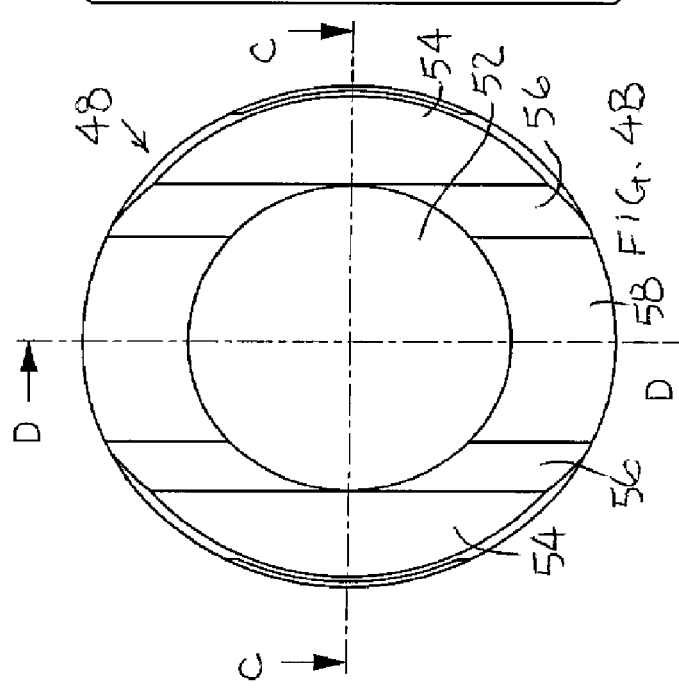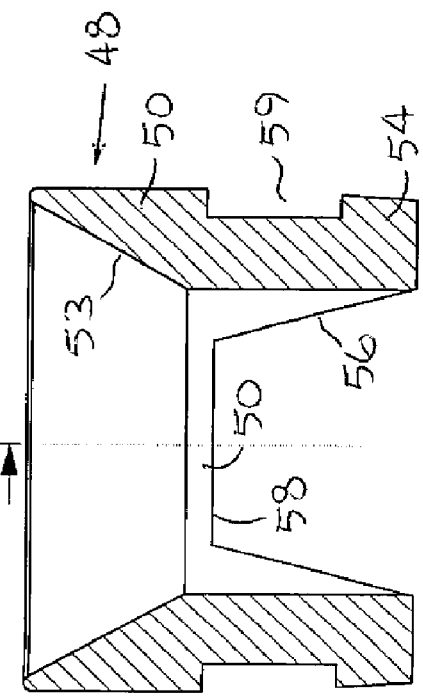
FIG. 4D
FIG. 4A
FIG. 4B
FIG. 4C

DOUBLE COLLET CONNECTOR ASSEMBLY FOR BONE ANCHORING ELEMENT

FIELD OF THE INVENTION

The present invention relates generally to anchoring structures for orthopedic devices, and particularly to a connector assembly for connecting rods and the like to bone anchoring elements, such as pedicle screws.

BACKGROUND OF THE INVENTION

Many spinal fixation systems are found in the prior art for fixing connecting rods and the like to pedicle screws. Some systems have a disadvantage in that the rod must be bent after coupling to the pedicle screw because of anatomical considerations. Some systems attempt to solve this problem with different kinds of connectors that secure the rod to a polyaxial pedicle screw head and permit spatial adjustments before locking the rod in place. It is imperative to lock the connecting rod with respect to the pedicle screw (or any other kind of bone anchoring element) in order to prevent loosening of the spinal fixation system that could have undesirable consequences to the patient. Nevertheless, no design is free of problems and there is still a need for a connector that is "user-friendly" and permits adjustments before locking the rod in place.

SUMMARY OF THE INVENTION

The present invention seeks to provide an improved connector assembly for connecting rods and the like to bone anchoring elements, such as pedicle screws, as is described more in detail hereinbelow. The connector assembly of the invention permits rotational and translational adjustments before locking the rod in place. The connector assembly of the invention includes a double collet assembly with enhanced wedging force.

There is thus provided in accordance with an embodiment of the present invention a connector assembly including a bone anchoring element including a spherical head, a double collet that includes an inner clamping portion formed by inner surfaces of a plurality of resilient fingers, the resilient fingers defining a first wedge surface and a second wedge surface, an outer closure element that includes an inner clamping portion that corresponds in shape to an outer contour of the double collet, the outer closure element including a pair of arms that define a channel shaped for receiving therein a connector element, and an interface ring that includes a base formed with an inner wedge surface and a pair of wing extensions that extend from the base.

In accordance with an embodiment of the present invention the inner clamping portion of the double collet is placed over the spherical head of the bone anchoring element, the interface ring is placed over the double collet so that the inner wedge surface sits against the first wedge surface, the outer closure element is placed over the interface ring and the double collet, wherein the inner clamping portion of the outer closure element abuts against the second wedge surface, and the connector element is placed in the channel of the outer closure element, and wherein the connector assembly further includes a cap member which is tightened against the connector element, which forces the connector element against the interface ring, which presses against the first wedge surface of the double collet, thereby causing the second wedge surface to be wedged between the outer closure element and the spherical head and also presses the first wedge surface onto the spherical head so that the double collet firmly grips the spherical head of the bone anchoring element.

Further in accordance with an embodiment of the present invention the connector element does not contact the spherical head of the bone anchoring element. The first and second wedge surfaces may be conical in shape. The resilient fingers may be separated from each other by grooves formed in the double collet.

The upper portion of the arms of the outer closure element may be threaded and the cap member may threadingly mate with the upper portion. The wing extensions may have inner sloping surfaces.

BRIEF DESCRIPTION OF THE DRAWINGS

The present invention will be understood and appreciated more fully from the following detailed description taken in conjunction with the drawings in which:

FIGS. 1A and 1B are simplified pictorial and sectional illustrations, respectively, of a connector assembly for a bone anchoring element, constructed and operative in accordance with an embodiment of the present invention;

FIGS. 2A, 2B, 2C and 2D are simplified pictorial, top view, sectional and side-view illustrations, respectively, of a double collet of the connector assembly of FIGS. 1A-1B, constructed and operative in accordance with an embodiment of the present invention;

FIGS. 3A, 3B, 3C and 3D are simplified front view, side view, sectional and thread detail view illustrations, respectively, of an outer closure element of the connector assembly of FIGS. 1A-1B, constructed and operative in accordance with an embodiment of the present invention;

FIGS. 4A, 4B 4C and 4D are simplified pictorial, top-view, side sectional and front sectional illustrations, respectively, of an interface ring of the connector assembly of FIGS. 1A-1B, constructed and operative in accordance with another embodiment of the present invention.

DETAILED DESCRIPTION OF EMBODIMENTS

Figure 5A:
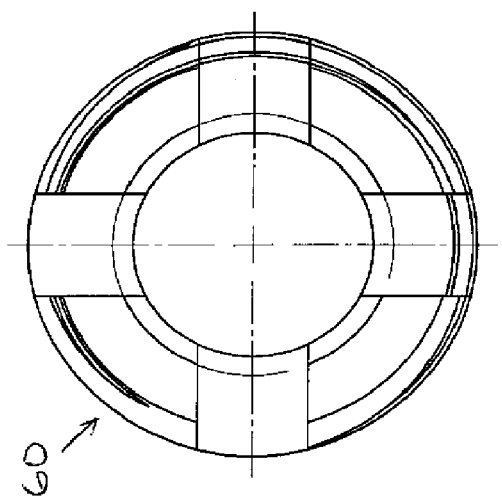
FIGS. 5A, 5B, 5C and 5D are simplified pictorial, top view, sectional and thread detail view illustrations, respectively, of a cap element of the connector assembly of FIGS. 1A-1B, constructed and operative in accordance with an embodiment of the present invention.

Reference is now made to FIGS. 1A-1B, which illustrate a connector assembly 10 for a bone anchoring element 12, constructed and operative in accordance with an embodiment of the present invention.

In a non-limiting embodiment of the invention, the bone anchoring element 12 includes a threaded mechanical fastener (for example, without limitation, a pedicle screw, a pedicle anchor device, a blocking screw for a pedicle anchoring device or any other device for attachment to the pedicle, vertebral body or any other bone) having a spherical proximal portion 14 (also referred to as a spherical head 14) and a (pointed) distal portion 16. Alternatively, bone anchoring element 12 can be a hook or other mechanical fastener with a spherical head. The spherical head 14 may be formed with a socket for an Allen wrench or the like.

Reference is now made additionally to FIGS. 2A-2D. The connector assembly 10 includes a double collet 18 that includes an inner clamping portion 20, formed by inner surfaces of a plurality of resilient fingers 22 (also referred to as tabs, leaves or petals, these terms and the like being used interchangeably) spaced around a longitudinal axis 24 thereof. Resilient fingers 22 are separated from each other and are formed by cuts or grooves 26 formed in double collet 18. The plurality of resilient fingers 22 of double collet 18 define two wedge surfaces 30 (first or upper wedge surface 30 in the sense of the drawing) and 32 (second or lower wedge surface 32). The wedge surfaces are angled with respect to each other and are preferably conical in shape. Clamping portion 20 resiliently clamps on spherical head 14 of bone anchoring element 12.

Reference is now made additionally to FIGS. 3A-3D. The connector assembly 10 may include an outer closure element 34 that includes an inner clamping portion 36 (FIG. 3C). The inner clamping portion 36 is preferably conical in shape, and corresponds to the outer conical contour of second wedge surface 32 of double collet 18. Outer closure element 34 may include a pair of arms 38 that define a channel 40 (FIGS. 3A and 3C), shaped to receive therein a connector element 42 (FIGS. 1A-1B). Channel 40 is preferably U-shaped, but other shapes are possible. An upper portion 44 (FIG. 3C) of arms 38 may be threaded. A pair of diametrically-opposed blind holes 46 may be formed on the outside of arms 38 so as to create inner dimples 39. Holes 46 may also be used for grasping outer closure element 34 with a grasping tool.

Reference is now made additionally to FIGS. 4A-4D. The connector assembly 10 may include an interface ring 48. Interface ring 48 may include a round base 50 with a hole 52 axially bored therethrough. Base 50 is formed with an inner wedge surface 53, formed such as by countersinking a conical surface. A pair of wing extensions 54 extend (upward in the sense of FIG. 4A) from base 50. The wing extensions 54 have inner sloping surfaces 56. A generally flat upper portion 58 of base 50 separates the wing extensions 54 from one another. Interface ring 48 may also be formed with a pair of diametrically-opposed flat indentations 59. During assembly of connector assembly 10, dimples 39 of outer closure element 34 are received ("click") in indentations 59.

The connector assembly 10 may be constructed of any suitable, medically safe material, such as but not limited to, stainless steel alloy (e.g., AISI 316L), titanium or titanium alloy or chrome cobalt alloy, PEEK (polyetheretherketone), shape memory alloys or polymers, including resorbable materials, or any combination of the above. Any material may be coated, such as with HA (hydroxyapatite), any factors or substances including active or passive antibiotics, etc. Different parts of connector assembly 10 may be constructed of different materials with different resilience or hardness, or of the same material but treated to have different resilience or hardness.

The connector element 42 is illustrated as a rod with a cylindrical cross section. However, the invention is not limited to this construction, and connector element 40 may be any slender elongate element, such as but not limited to, a bar of hexagonal, rectangular or square cross section, a rod of elliptical cross section, and many others.

Assembly of connector assembly 10 is straightforward and easy. Referring to FIG. 1B, after bone anchoring element 12 (e.g., pedicle screw) is in place, the user places the inner clamping portion 20 of double collet 18 over spherical head 14 of bone anchoring element 12. Interface ring 48 is then placed over double collet 18 so that the inner wedge surface 53 sits against the first (upper) wedge surface 30 of resilient fingers 22. The outer closure element 34 is then placed over interface ring 48 and double collet 18. The inner clamping portion 36 of outer closure element 34 abuts against the second (lower) wedge surface 32 of resilient fingers 22. At this point, the hexagonal socket of spherical head 14 is still accessible for tightening with a wrench or other tool, because all the parts of the connector assembly have through holes for accessing spherical head 14.

The connector element 42 is then placed in U-shaped channel 40 of outer closure element 34. It is noted that connector element 42 also passes through the gap between arms 54 of interface ring 48. It is further noted that the upper portion 58 of base 50 is slightly higher than the bottom of U-shaped channel 40 so that connector element 42 abuts against base 50 of interface ring 48 and not against outer closure element 34. A threaded cap member 60 is then screwed on the upper portion 44 of arms 38 of outer closure element 34. Cap member 60 is tightened against connector element 42. This forces connector element 40 against the upper portion 58 of base 50 of interface ring 48, which slides on and presses downwards (in the sense of the drawing) against the first wedge surface 30 of resilient fingers 22 of double collet 18. This downward force has two wedging actions. First, the downward force causes the second wedge surface 32 to be wedged between outer closure element 34 and spherical head 14. This squeezes and clamps the lower portion of resilient fingers 22 (second wedge surface 32) onto spherical head 14 of bone anchoring element 12. Second, the downward force presses the upper portion of resilient fingers 22 (first wedge surface 30) onto the top of spherical head 14 of bone anchoring element 12. The double clamping action makes the double collet 18 firmly grip spherical head 14 of bone anchoring element 12. There is no contact between connector element 42 and spherical head 14 of bone anchoring element 12.

An auxiliary cap element 62 may be threadedly received in inner threads of cap member 60. The auxiliary cap element 62 may be used to further clamp down on connector element 42 and provide a fine adjustment of the force thereupon.

Figure 5C:
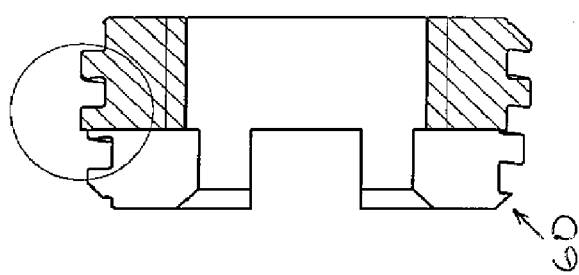
Figure 5B:
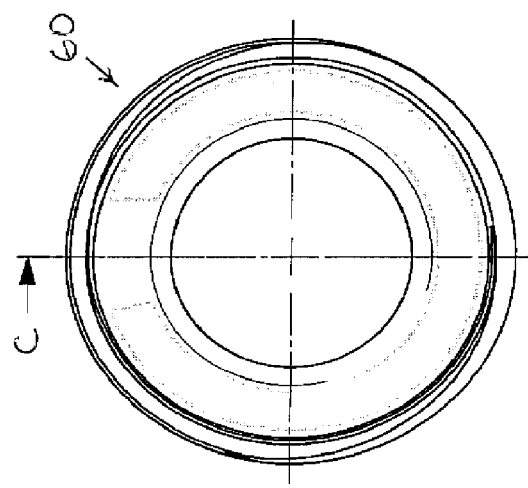
Figure 5D:
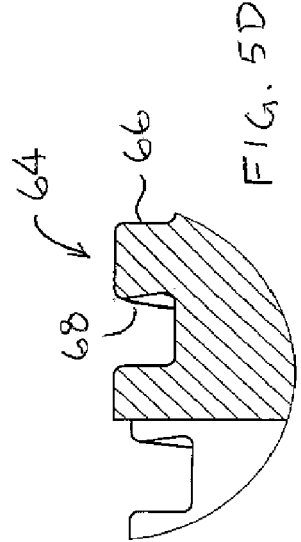

Reference is now made additionally to FIGS. 5A-5D. Instead of convention threads, cap element 60 may be formed with a thread 64 that comprises one flat side 66 and an opposite side 68 which is not parallel to flat side 66 but is angled about 10° thereto. This specially formed thread 64, when tightened in complimentary female threads formed in upper portion 44 (FIG. 3C) of arms 38 of outer closure element 34, tends to pull arms 38 inwards. This prevents cap element 60 from tending to force the arms 38 outwards, which would play against the desired tightening force on connector element 42.

The connector assemblies of the invention permit rotational adjustments with respect to the spherical head of the bone anchoring element and translational adjustments of the connector element before locking the connector element in place.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A connector assembly comprising:
   a bone anchoring element comprising a spherical head;
   a double collet that comprises an inner clamping portion formed by inner surfaces of a plurality of resilient fingers, said resilient fingers defining a first wedge surface and a second wedge surface;
   an outer closure element that comprises an inner clamping portion that corresponds in shape to an outer contour of said double collet, said outer closure element comprising a pair of arms that define a channel shaped for receiving therein a connector element;

an interface ring that comprises a base formed with an inner wedge surface and a pair of wing extensions that extend from said base; and a cap element that threadingly mates with threads formed on said arms, wherein said cap element is formed with a thread that comprises one flat side and an opposite side which is not parallel to said flat side, wherein said flat side and said opposite side of said thread, when tightened in complimentary female threads formed in said arms of said outer closure element, pull said arms inwards.

2. The connector assembly according to claim 1, wherein said opposite side is angled about 10° said flat side.

* * * * *